United States Patent
Goldbard et al.

(10) Patent No.: US 6,524,798 B1
(45) Date of Patent: Feb. 25, 2003

(54) HIGH EFFICIENCY METHODS FOR COMBINED IMMUNOCYTOCHEMISTRY AND IN-SITU HYBRIDIZATION

(75) Inventors: Simon Goldbard, San Jose; Tsai-Hsia Hong, San Mateo; Michael A. Zoccoli, Moraga; Emily Lin, San Jose, all of CA (US)

(73) Assignee: Applied Imaging Corporation, Santa Clara, CA (US)

( * ) Notice: Subject to any disclaimer, the term of this patent is extended or adjusted under 35 U.S.C. 154(b) by 167 days.

(21) Appl. No.: 09/592,120

(22) Filed: Jun. 12, 2000

Related U.S. Application Data

(60) Provisional application No. 60/140,267, filed on Jun. 18, 1999.

(51) Int. Cl.[7] ...................... G01N 33/53; G01N 33/542; C07H 21/04; C07H 21/02
(52) U.S. Cl. .............................. 435/6; 435/7.1; 435/7.5; 435/7.9; 536/24.31; 536/25.32
(58) Field of Search .............................. 435/6, 7.1, 7.9, 435/7.5; 536/24.31, 25.32

(56) References Cited

U.S. PATENT DOCUMENTS 5,328,985 A  7/1994  Sano et al. .................. 530/350

OTHER PUBLICATIONS

Herbergs, J., et al., "Combination of lamin immunoctyochemistry and in situ hybridization for the analysis of chromosome copy numbers in tumor cell areas with high nuclear density", *Cytometry*, 23(1):1–7, (1996).

Kraus, J., et al., "Tumorigenic and micrometastatic potential and cytogenetic characterization of immunocytochemically identified micrometastatic cells", *Proc. of the American Association of Cancer Research Annual Meeting*, 40:711 (1999).

Laufer, M., et al., "Detection and characterization of circulating prostate cancer cells: A potential clinical tool for the management of advance prostate cancer", *Journal of Urology*, 161(4):299, (1999).

Lavarino, C., et al., "Detection of TP53 mutation, loss of heterozygosity and DNA content in fine–needle aspirates of breast carcinoma", *Br. J. Cancer*, 77(1):126–130, (1998).

Litle, V. R., et al., "Molecular cytogenetic analysis of cytokeratin 2–labeled cells in primary tumors and bone marrow aspirates from colorectal carcinoma patients"" *Cancer*, 79(9):1664–1670, (1997).

Mialhe, A, et al., "Methods for Simultaneous Interphase In Situ Hybridization and Nuclear Antigen Immunocytochemistry in T47–D Cells", *The Journal of Histochemistry and Cytochemistry*, 44:193–197, (1996).

Neft, R. E., et al., Concurrent Fluorescence in Situ Hybridization and Immunocytochemistry for the Detection of Chromosome Aberrations in Exfoliated Bronchial Epithelial Cells, *Acta Cytologica*, 41:1769–1773, (1997).

O'Connor, S. J., et al., "The rapid diagnosis of acute promyelocytic leukaemia using PML (5E10) monoclonal antibody", *Br. J. Haematol*, 99(3):597–604 (1997).

Oosterwijk, J.C., et al., "Detection of fetal erythroblasts in maternal blood by one–step enrichment, immunocytochemical recognition, FISH analysis and automated microscopy", *Amer Jour of Human Gen*, 59(4):A327, (1996).

Oosterwijk, J.C., et al., "Development of a Preparation and Staining Method for Fetal Erythroblasts in Maternal Blood: Simultaneous Immunocytochemical Staining and FISH Analysis", *Cytometry*, 32:170–177, (1998).

Oosterwijk, J.C., et al., "Fetal cell detection in maternal blood: A study in 236 samples using erythroblast morphology, DAB and HbF staining, and FISH analysis", *Cytometry*, 32(3):178–185, (1998).

Oosterwijk, J.C., et al., "Strategies for Rare–Event Detection: An Approach for Automoated Fetal Cell Detection in Maternal Blood", *Am. J. Hum. Genet.*, 63:1783–1792, (1998).

Pazouki, S., et al., "A rapid combined immunoctyochemical and fluorescence in situ hybridisation method for the identification of human fetal nucleated red blood cells", *Acta Histochem*, 98(1):29–37, (1996).

Persons, D. L., "Quantiation of HER–2/neu and c–myc gene amplification in breast carcinoma using fluorescence in situ hybridization", *Mod Pathol*, 10(7):720–7, (1997).

Schouten, H. C., et al., "Large–cell anaplastic non–Hodgkin's lymphoma originated in donor cells after allogenic bone marrow transplantation", *Br. J. Haematol*, 91(1):162–6, (1995).

Speel, E.J.M., et al., "Cytochemical detection systems for in situ hybridization, and the combination with immunocytochemistry. 'Who is still afraid of Red, Green and Blue?'", *Histochemical Journal*, 27:833–858, (1995).

Zheng, Y., et al., "Prenatal diagnosis from maternal blood: simultaneous immunophenotyping and FISH of fetal nucleated erythrocytes isolated by negative magnetic cell sorting", *H. Med. Genet.*, 30:1051–1056, (1993).

*Primary Examiner*—W. Gary Jones
*Assistant Examiner*—Joyce Tung
(74) *Attorney, Agent, or Firm*—Townsend and Townsend and Crew LLP

(57) ABSTRACT

The invention provides a high efficiency method for combined immunocytochemistry and in situ hybridization. In one aspect, the method is used to simultaneously determining a cell phenotype and genotype by contacting a cell with an antigen-specific antibody bound to a ligand, contacting the cell with polynucleotide probe to form a complex of the probe and a nucleic acid in the cell, contacting the cell with a detectably labeled anti-ligand, and detecting the polynucleotide-probe complex and the anti-ligand-ligand complex. The presence of the anti-ligand is correlated with the presence of the antigen and the presence of the probe-nucleic acid complex is correlated with the presence of the nucleic acid in the cell.

27 Claims, No Drawings

HIGH EFFICIENCY METHODS FOR COMBINED IMMUNOCYTOCHEMISTRY AND IN-SITU HYBRIDIZATION

This application claims benefit of No. 60/140,287, filed Jun. 18, 1999.

FIELD OF THE INVENTION

This invention relates to new methods for characterizing the genotype and phenotype of a cell in a sample, and finds application in medicine, genetics, histology, developmental biology and cell biology.

BACKGROUND OF THE INVENTION

Determination of cell phenotype by immunophenotyping or immunocytochemistry (ICC) and determination of cell genotype using hybridization-based methods (e.g., in situ hybridization assays, "ISH") are important processes in the diagnosis and study of disease. Although both ISH and ICC have been widely used for analysis, they have only infrequently been used in combination (e.g., on the same cells or different aliquots of cells from a sample). In part this is because the methods now available for simultaneously determining phenotype by antibody staining and determining genotype by ISH are cumbersome, inefficient, and of limited accuracy.

The conditions required for ISH and ICC are generally incompatible or non-optimal for the practice of the other. Carrying out ISH analysis following ICC may be inefficient due to the blocking effects of the reporting molecules used in ICC (e.g., substrate precipitate or fluorochromes). Conversely, carrying out ISH prior to ICC is unsatisfactory, e.g., because the elevated temperature and denaturation steps used for ISH are not compatible with subsequent ICC. Thus, attempts to carry out the two methods in combination have been limited. Neft et al., 1997, *Acta Cytologica* 41:1769–1773, carried out ISH after ICC staining for the intermediate filament protein (cytokeratin). In this study, centromeric repetitive sequences from chromosome 7 were used for the ISH DNA probes, but no data relating to hybridization efficiency and accuracy were provided. Schouten et al., 1995, *Brit. J. Haematology* 91:162–166, described the use of ISH with RNA probes in combination with anti-CD30 immunocytochemistry. They reported low efficiency in identifying Y chromosome containing cells and poor results when using multiple different ISH probes. Pazouki et al. 1996, *Acta histochem* (*Jena*) 98:29–37 described using ICC with an anti-hemoglobin antibody and a second-antibody detection system followed by ISH using repetitive-sequence probes (from chromosome X and Y centromeric sequences) to identify fetal cells. However, the authors provided no information on the efficiency of the method or the number of cells correctly typed.

None of these references provided a method that is specific and accurate when used for immunostaining of many types of cell antigens (e.g., cytoplasmic, membrane-associated, etc.) and many types of ISH probes (e.g., centromeric probes and unique sequence probes).

The present invention provides new and surprisingly efficient methods for analysis of cell phenotype and genotype, which may be carried out on the same cells in a sample.

SUMMARY OF THE INVENTION

In one aspect, the invention provides a method of simultaneously determining a cell phenotype and genotype by:

(a) contacting the cell with an antibody bound to a ligand, wherein the antibody is specific for an antigen suspected of being associated with the cell;
(b) contacting the cell with polynucleotide probe under conditions that allow the probe to hybridize to a target sequence in a cellular nucleic acid, thereby forming a complex of the polynucleotide probe and cellular nucleic acid;
(c) contacting the cell with a detectably labeled anti-ligand under conditions where the detectably labeled anti-ligand binds to the ligand;
(d) detecting the presence of the labeled anti-ligand;
(e) detecting the presence of the complex of the polynucleotide probe and cellular nucleic acid; and,
(f) correlating the presence of the anti-ligand with the presence of the antigen in the cell thereby determining the cell phenotype, and correlating the presence of said complex of the polynucleotide probe and cellular nucleic acid with the presence of the target sequence in the cell, thereby determining the cell genotype. According to the invention, step (a) of the method precedes step (b), and step (b) precedes step (c).

In preferred embodiments, the cell is exposed to a fixative between step (a) and step (b).

In various embodiments of the method, the cell is a human cell, such as a human fetal cell; the antibody is monoclonal; the ligand is biotin; the anti-ligand is avidin or streptavidin, which may be labeled with a reporter molecule that is fluorescent, a radioisotope, or an enzyme; the antigen is hemoglobin; and/or the polynucleotide probe is DNA, such as a probe that specifically hybridizes to sequences of human chromosomes X, Y. 13, 18 or 21. In some embodiments of the invention, signal detection is accomplished by microscope analysis.

In certain embodiments, the disclosed method is used to detect or diagnose a chromosomal abnormality in a fetal cell, a malignant cell, or a cell suspected of being malignant.

In a related aspect, the invention provides a method of simultaneously determining a cell phenotype and genotype comprising:

(a) contacting the cell with an antibody specific for an antigen suspected of being associated with the cell;
(b) contacting the cell with polynucleotide probe under conditions that allow the probe to hybridize to a target sequence in a cellular nucleic acid, thereby forming a complex of the polynucleotide probe and cellular nucleic acid;
(c) contacting the cell with a binding molecule that specifically binds the antibody of step (a);
(d) detecting the presence of the binding molecule;
(e) detecting the presence of the complex of the polynucleotide probe and cellular nucleic acid; and,
(f) correlating the presence of the binding molecule with the presence of the antigen in the cell thereby determining the cell phenotype, and correlating the presence of said complex of the polynucleotide probe and cellular nucleic acid with the presence of the target sequence in the cell, thereby determining the cell genotype. Step (a) of the invention precedes step (b), and step (b) precedes step (c). In preferred embodiments, the cell is exposed to a fixative between step (a) and step (b).

In various embodiments of the invention, the binding molecule is an anti-immunoglobulin antibody, protein A or protein G, which may be detectably labeled, for example with a reporter molecule that is fluorescent, a radioisotope, or an enzyme.

In various embodiments of the method, the cell is a human cell, such as a human fetal cell; the antibody is monoclonal; the antigen is hemoglobin; and/or the polynucleotide probe is DNA, such as a probe that specifically hybridizes to sequences of human chromosomes X, Y, or 21.

The invention further provides kits useful for practicing the combined immunocytochemistry and in situ hybridization method of the invention.

DETAILED DESCRIPTION

I. Introduction

In one aspect, the invention provides a highly efficient method for determining the phenotype and genotype of a cell by carrying out both antibody staining to detect antigens in the cell or population (e.g., immunocytochemistry) and in situ hybridization to determine the genetic composition or karyotype of the cell.

Although methods for carrying out ISH and ICC are well established, the art lacks efficient and effective methods for carrying out ISH and ICC on the same cells. For optimal utility in diagnostic and research applications, a combined ICC/ISH method, should work with antigens from different cell compartments (e.g., cytoplasmic, extracellular, etc.), should be amenable to use with both repetitive-sequence and non-repetitive-sequence ISH probes, and should be highly specific and accurate.

In one aspect of the invention disclosed here, cells are analyzed by binding a cell-antigen specific antibody to a target cell, exposing the cell to a fixing agent, carrying out ISH on the cell, and subsequently detecting the antibody bound to the cell antigen. The bound antibody can be detected using a reporter molecule that binds (e.g., through an anti-ligand) to a ligand associated with the cell-antigen specific antibody. Alternatively, the bound antibody (i.e., the primary antibody) can be detected using a detectably labeled secondary antibody that specifically binds the bound cell-antigen-specific antibody. For example, a detectably labeled anti-immunoglobulin antibody can serve as the secondary antibody.

Because the present method is accurate and convenient, it is useful in a variety of clinical and research applications. In particular, the method is useful in the fields of prenatal screening of genetic traits and in cancer diagnosis. For example, in the case of prenatal diagnostics, fetal cells may be obtained by chorionic villus sampling (CVS), by amniocentesis, or from maternal blood (see, e.g., Oosterwicjk et al., 1998, *Am. J. Hum. Genet.* 63:1783–92), and analyzed by the method of the present invention. By way of non-limiting example, when cells are obtained from maternal blood, immunophenotyping may be used to distinguish fetal cells from maternal calls, and ISH may be used to determine chromosome copy number in the fetal cells.

In the case of cancer diagnosis, it is often desirable to distinguish a malignant cell from non-malignant cells in a sample, and to detect chromosome aberrations in the malignant cell. According to the present invention, a phenotypic marker can be used to identify a malignant cell (e.g., cytokeratin may be used as a marker for epithelial lineage cancers, such as breast, gastric, lung, prostate, esophageal, ovarian, colorectal and endometrial cancers), and ISH techniques used to identify chromosome aberrations, gene expression patterns, or the presence of viral sequences. Many other applications of the present method will be immediately apparent to those of skill upon review of this disclosure.

In Section II, infra, a number of terms are defined to provide guidance to one of skill in the practice of the invention. In Section III, the methods of the invention are described in some detail. Section IV provides examples of the practice of the invention.

II. Definitions a) Immunophenotyping

As used herein, the terms "immunophenotyping" and "antibody staining" are used interchangeably to refer to the use of antibodies (as defined below) that specifically bind a cell antigen to characterize the phenotype of the cell. The antibody binding may be detected directly or indirectly, including by use of enzymatic reporter molecule (e.g., a phosphatase such as alkaline phosphatase, a peroxidase such as horseradish peroxidase, and the like) that acts on a substrate to produce a detectable product to detect the antibody. Alternatively, a fluorescent or radioactive reporter molecule, or other methods may be used. As used herein, "immunocytochemistry (ICC)" refers to immunophenotyping carried out on a substrate (e.g., a slid e or the equivalent) in which a microscope is used for analysis, often in conjunction with an automated image analysis system.

b) In Situ Hybridization (ISH)

As used herein "in situ hybridization (ISH)" refers to hybridization of a polynucleotide probe to the chromosomal DNA or mRNA in a cell. The probe may be RNA, DNA, PNA (peptide nucleic acid), a chimeric nucleic acid (e.g., a DNA-RNA chimera) or the like. In preferred embodiments nonisotopic ISH is carried out. The most widely used ISH method is "fluorescence in situ hybridization" or "FISH," in which the probe is detected by fluorescein-12-dUTP are used (Wiegant et al., 1991, *Nuc. Acid. Res.* 372:809–812). Other examples of suitable labels include Spectrum Orange-dUTP, Spectrum Green-dUTP; Spectrum Red-dUTP and others known in the art or to be discovered in the future (see, e.g., Vysis Inc. 1999 Catalog, incorporated herein in its entirety by reference). Alternatively, biotin- or digoxigenin-labeled DNA probes are used and are visualized using reagents such as fluorochrome-conjugated avidin, streptavidin, or anti digoxigenin.

A variety of variants of the basic ISH technique are well known, and the use of these techniques in conjunction with the present invention is contemplated. ISH techniques include, but are not limited to "M-FISH" (Connor and Ferguson-Smith, 1997, *Essential Medical Genetics,* Blackwell Science Eds. p. 86–87); "Poly-FISH" (see, e.g., Zhen et al., 1998, "Poly-FISH: a technique of repeated hybridizations that improves cytogenetic analysis of fetal cells in maternal blood" *Prenat. Diagn.* 18:1181–1185); "PRINS" (see, e.g., Adinoffi and Davies, 1994, "NISH and PRINS Methods" in Nonisotopic in-situ Hybridization, R. G. Landes Company, Austin, Tex. 17–38); "Interphase FISH" (see, e.g., Oosterwijk et al., 1998, "Development of a preparation and staining method for fetal erythroblasts in maternal blood: simultaneous immunocytochemical staining and FISH analysis," *Cytometry* 32:170–177); "Chromosome banding" (see, e.g., Muller et al., 1997, "Toward a multicolor chromosome bar code for the en tire human karyotype by FISH" *Hum. Genetics* 100:271–78). Also see, Bohmeret al., 1998, "Differential development of fetal and adult heamoglobin profiles in colony culture: isolation of fetal nucleated red cells by two-color fluorescence labeling," *British Journal of Haematology* 103: 351–360; and Xu et al., 1998, "Improving the fixation method for preimplantation genetic diagnosis by fluorescent in situ hybridization," *Journal of Assisted Reproduction and Genetics* 15 (9) :570–574.

c) Antibody

As used herein, "antibody" refers to a human, nonhuman, or chimeric (e.g., humanized) immunoglobulin, or binding fragment thereof, that specifically binds to an antigen (e.g., an antigen in a cell). Suitable antibodies may be polyclonal (e.g., sera or affinity purified preparations), monoclonal, or recombinant. Useful fragments include separate heavy chains, light chains, Fab, Fab' F(ab')2, Fabc, and Fv fragments. Fragments can be produced by enzymatic or chemical separation of intact immunoglobulins or by recombinant DNA techniques. Often fragments are expressed in the form of phage-coat fusion proteins (see, e.g., Dower et al., WO 91/17271 McCafferty et al., WO 92/01047; and Huse, WO 92/06204). Typically, the antibodies, fragments, or similar binding agents bind a specific antigen with an affinity of at least $10^7$, $10^8$, $10^9$, or $10^{10} M^{-1}$.

Methods of preparing, manipulating, labeling, and using antibodies are well known in the art. See, e.g., Harlow and Lane, 1988, *Antibodies: A Laboratory Manual,* Cold Spring Harbor Laboratory, New York (hereinafter "Harlow") and Ausubel et al., 1999, *Current Protocols In Molecular Biology* Greene Publishing and Wiley-Intescience, New York, including *Supplement* 46 (April 1999) (hereinafter "Ausubel"), both of which are incorporated herein by reference. Many suitable antibodies are available commercially, see, e.g., Cortex Biochem, Inc. (San Leandro Calif.), Becton-Dickinson Immunocytometry Systems (San Jose, Calif.), Pharmingen (San Diego Calif.), Caltag Laboratories, Inc. (Burlingam Calif.), DAKO Corp. (Carpinteria Calif.).

As used herein, the term "primary antibody" is sometimes used to refer to an antibody that binds the cellular antigen of interest, e.g., as distinguished from a "secondary antibody" which is an anti-antibody antibody sued for indirect detection of a primary antibody.

d) Specific Binding

As used herein, "specific binding" refers to the ability of one molecule, typically an antibody or polynucleotide, to contact and associate with another specific molecule even in the presence of many other diverse molecules. For example, a single-stranded polynucleotide can specifically bind to a single-stranded polynucleotide that is complementary in sequence, and an antibody specifically binds to (or "is specifically immunoreactive with") its corresponding antigen.

e) Cell Phenotype

As used herein, "cell phenotype" has its ordinary meaning and refers to characteristics displayed by a cell, especially the expression of a particular complement of proteins, under a particular set of environmental factors, regardless of the actual genotype of the organism.

f) Cell Genotype

As used herein, "cell genotype" refers to the genetic or chromosomal complement of a cell. Information about the cell genotype includes the detection of chromosome number, the detection of any chromosome aberrations, or the detection of specific nucleotide sequence (e.g., gene sequences, genetic markers, polymorphisms, and the like) in a cell.

g) Expression Profile

As used herein, the term "expression profile" of a cell refers to the RNAs (mRNAs) expressed in the cell. Particular RNAs may be detected by ISH techniques.

h) Pathogen Profile

As used herein, the term "pathogen profile" refers to the presence of viral, bacterial, fungal or other pathogens for which pathogen-specific nucleic acids can be detected by ISH specific probes.

i)n Ligand and Anti-ligand

As used herein, the terms "ligands" and "anti-ligand" refer to pairs of molecules that specifically bind to each other. Exemplary ligand/anti-ligand pairs include any haptenic or antigenic compound in combination with an antibody (e.g., digoxigenin and anti-digoxigenin; mouse immunoglobulin and goat anti-mouse immunoglobulin) as well as non-immunological binding pairs (e.g., biotin-avidin, biotin-streptavidin, hormone-hormone receptors, IgG-protein A, and the like).

j) Detectably Labeled

As used herein, "detectably labeled" has the ordinary meaning in the art. A molecule (e.g., antibody or polynucleotide probe) can be detectably labeled by virtue of containing an atom (e.g., radionuclide), molecule (e.g., fluorescein), or complex, that due to a physical or chemical property, indicate the presence of the molecule. A molecule is also detectably labeled when it is covalently bound or otherwise associated with a "reporter" molecules (e.g., a biomolecule such as an enzyme) that act on a substrate to produce a detectable atom, molecule complex. Detectable labels suitable for use in the present invention include any composition detectable by spectroscopic, photochemical, biochemical, immunochemical, electrical, optical or chemical means. Labels useful in the present invention include biotin for staining with labeled avidin or streptavidin conjugate, magnetic beads (e.g., Dynabeads TM), fluorescent dyes (e.g., fluorescein, fluorescein-isothiocyanate [FITC], Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SyBR Green I & II [Molecular Probes], and the like), radiolabels (e.g., $^3H$, $^{125}I$, $^{35}S$, $^{14}C$, or $^{32}P$), enzymes (e.g., hydrolases, particularly phosphatases such as alkaline phosphatase, esterases and glycosidases, or oxidoreductases, particularly peroxidases such as horse radish peroxidase, and the like), substrates, cofactors, inhibitors, chemiluminescent groups, chromogenic agents, and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels and chemiluminescent labels may be detected using photographic film or scintillation counters, fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and colorimetric labels are detected by simply visualizing the colored label. Means of detecting labels are well known to those of skill in the art. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the color associated with the label.

It will be appreciated that, in the practice of the invention, although not absolutely necessary, generally different labels will be used for antibody staining and ISH, so that the different probes can be easily distinguished. For example, when both a polynucleotide ISH probe and the labeled anti-ligand probe are labeled with fluorophores, it is generally preferred that they have distinct emission patterns (wavelengths) so that they can be easily distinguished.

k) "Chromosome-specific probe" or "chromosome-specific paint" refers to a combination of detectably labeled polynucleotides that have sequences corresponding to (e.g., essentially the same as) the sequences of DNA from a particular chromosome or subchromosomal region of a particular chromosome (e.g., a chromosome arm). Typically, the chromosome-specific probe is produced by amplification (e.g., using the polymerase chain reaction) of the corresponding chromosomal DNA. A chromosome-specific probe will hybridize in an essentially uniform pattern along the chromosome or subchromosomal region from which it is derived.

l) Karyotype

As used herein, the term "karyotype" has its normal meaning and refers to the chromosome characteristics of an individual cell or cell line of a given species, as defined by both the number and morphology of the chromosomes. Typically, the karyotype is presented as a systematized array of prophase or metaphase (or otherwise condensed) chromosomes from a photomicrograph or computer-generated image. Alternatively, interphase chromosomes may be examined as histone-depleted DNA fibers released from interphase cell nuclei.

m) Chromosome Abnormality

As used herein, "chromosomal aberration" or "chromosome abnormality" refers to a deviation between the structure of the subject chromosome or karyotype and a normal (i.e., "non-aberrant") homologous chromosome or karyotype. The terms "normal" or "non-aberrant," when referring to chromosomes or karyotypes, refer to the predominate karyotype or banding pattern found in healthy individuals of a particular species and gender. Chromosome abnormalities can be numerical or structural in nature, and include aneuploidy, polyploidy, inversion, translocation, deletion, duplication, and the like. Chromosome abnormalities may be correlated with the presence of a pathological condition (e.g., trisomy 21 in Down syndrome, chromosome 5p deletion in the cri-du-chat syndrome, and a wide variety of unbalanced chromosomal rearrangements leading to dysmorphology and mental impairment) or with a predisposition to developing a pathological condition.

n) Binding Molecule

As used herein the term "binding molecule" when used to refer to the detection of an antibody (e.g., an antibody probe bound to a cell antigen) refers to a protein that specifically binds to a class of antibodies, e.g., protein A, protein G, an anti-immunoglobulin antibody (e.g., a goat anti-mouse antibody antibody), or the equivalent.

o) Efficiency and Accuracy

As used herein, the term "efficiency" refers to the ability of a given probe (antibody or polynucleotide) to enter a cell and stain the antigen or DNA (e.g., chromosome) in the cell. Efficiency is usually expressed as a percentage of the total number of target-antigen or target-chromosome containing cells in a sample, in which the probe signal can be detected.

As used herein, the term "accuracy," when referring to ISH analysis to detect chromosomes, refers to the ability to detect hybridization of the ISH probe in a cell and to detect a number of distinct signals per cell reflective of the number of target chromosomes in the cell (e.g., the number of different chromosomes containing the probe sequence). Alternatively, when distinct signals are not detected (e.g., when cells are analyzed in solution by FACS), "accuracy" refers to the ability to detect an intensity of signal reflective of the number of target molecules (e.g., the number of different chromosomes containing the probe sequence).

It will be appreciated that the results of antibody staining and ISH analysis are inherently dependent of the nature of the probe. In particular, ISH analysis of chromosome number normally produce a distribution of signal numbers. For example, in population of female cells all containing two X-chromosomes, the results of ISH using an X-chromosome probe will include cells with two signals, three signals, one signal, etc, with usually the correct number of signals (i.e., two, in this example) being detectable in the majority of cells. Thus, one way to assess the accuracy and efficiency of the method of combined immunophenotyping and genotyping disclosed herein is to compare the results (efficiency and accuracy) according to the present method with those obtained by conducting ICC and/or ISH separately using the same probes and cells. When probes are obtained commercially, the efficiency and accuracy are generally provided by the manufacturer.

III. Description

In this section, certain aspects of the invention are described. For convenience, the methods of the invention are discussed as series of steps. However, it will be understood that numerous variations may be carried out at each step without departing from the scope of the present invention.

A. Antibody Binding

In one step of the invention, a cell (or, usually, a plurality of cells) is contacted with an antibody that is specific for an antigen associated with, or suspected of being associated with, the cell or cells, so as to allow the antibody to bind the antigen.

The choice of cell and methods of preparing the cell will vary according to the particular needs of the practitioner. The method of the invention may be carried out with virtually any cell (e.g., mucleated cells) including but not limited to normal human cells, malignant or transformed cells, blood cells, fetal cells, cultured cells, biopsy samples, cryosections, touch preparations prepared from uncultured primary tumors, and the like. Cells may be obtained from aspiration biopsy or cells in bodily fluids (e.g., blood, urine, sputum and the like), amniotic fluid, maternal blood, and the like.

Typically the cell(s) are arrayed on a glass or plastic slide, coverslip, plastic dish and the like (i.e., a solid support), although this is not required. For example, the antibody may be contacted with cells in solution and the cells subsequently adhered to a support. In alternative embodiments, the entire process of ICC and ISH can be carried out in solution, and the cells deposited on a slide for microscope-based analysis, or, alternatively analyzed by flow cytometry.

Suitable methods of cell or tissue preparation and for binding antibodies to antigens include those used for conventional immunocytochemistry, and are well known in the art. See, for example, Harlow, supra, at Chapter 10. Immunophenotyping (e.g., ICC) techniques are known in the art and well within the capacity of one of ordinary skill to apply. See, e.g., Staines, 1988, *J. Histochem. Cytochem.* 36:145; Gillitzer et al., 1990, *J. Histochem. Cytochem.* 38:307; Wagner and Worman, 1988, *Stain Technology* 63:129; McGovern and Crocker, 1987, *Am. J. Clin. Pathol.* 88, 480; Graham et al., 1991, *J. Clin. Pathol.* 44:96; MaWhinney et al., 1990, *J. Clin. Pathol.* 43:591. Typically, the cells of interest are fixed (e.g., in buffered formalin) or permeablized (e.g., using by agents such as buffered detergent solution, e.g., Tween 20, Triton X, or NP 40 [<0.5% v/v] in Tris- or phosphate based buffers). Fixation or permeabilization is particularly preferred when the target antigen is not an extracellular protein (e.g., when the target is a cytoplasmic protein) to increase the accessibility of the antigen to the antibody. According to normal protocols, following antibody binding to the sample, any unbound antibody is removed in a wash step, e.g., PBS (phosphate buffered saline) or Tris-based buffer with or without non-ionic detergent.

Virtually any cell-associated antigen may be detected for example, without limitation, cytoplasmic antigens ($\gamma$-hemoglobin, $\epsilon$-hemoglobin, cytokeratin), nuclear antigens (PCNA [proliferating cell nuclear antigen]), disease-associated antigens (e.g., tumor markers, HER2/neu, p53), age- or developmental stage antigens (e.g., e.g. fetal hemoglobin vs adult hemoglobin), and pathogen-associated antigens (e.g., Epstein-Barr virus, Hepatitus B virus, HIV). One advantage of the present invention is that it is effective in detecting soluble cytoplasmic proteins (e.g., hemoglobin) and membrane or extracellular proteins, as well as highly stable proteins such as cytokeratin.

According to the invention, the bound antibody is detected by detection of a label that becomes associated with the bound antibody after the ISH step is carried out. Detection of the bound antibody may be accomplished in a number of ways. In one embodiment of the invention, the antibody (e.g., the "primary antibody") is conjugated to a ligand (e.g., biotin). As is explained in greater detail below, the ligand may be bound in subsequent steps with a detectably labeled anti-ligand, so that the presence of the antigen may be detected by the associated label. A wide variety of ligands may be used, and it will be understood the choice of ligand dictates the subsequent choice of anti-ligand.

One exemplary ligand is biotin (for which, e.g., avidin and streptavidin may act as anti-ligand). Biotin is particularly useful for several reasons, including the high affinity of avidin and streptavidin for biotin, and the signal amplification possible because a large number of biotin molecules can be conjugated to a protein or nucleic acid. A number of ligands and anti-ligands can be used, including, e.g., haptenic or antigenic compound used in combination with an antibody (e.g., digoxigenin and antibody, fluorescein-isothiocyanate (FITC) and anti-FITC antibody; dinitrophenol (DNP) and anti-DNP antibody), protein A or protein G in combination with an antibody, and the like.

In another embodiment of the invention, the "primary" antibody is not conjugated to a ligand and is instead detected using a secondary antibody (i.e., an anti-antibody antibody such as a goat anti-mouse IgG antibody) which is itself labeled or otherwise detectable. In a similar embodiment, a primary antibody bound to antigen is detected by contacting the antibody with detectably labeled protein A or protein G, following the ISH step.

Numerous strategies for amplification or indirect detection of antibodies are known. See, e.g., Ausubel at Chapter 14, and the use of such methods is contemplated in the practice of the present invention. It will be apparent to those of skill that cells may be stained with multiple antibodies.

B. Fixation

In preferred embodiments of the invention, the cell(s) or tissue sample is treated with a fixative following the binding of the antibody. Such fixation has been observed to dramatically improve the ability to detect stained cells. Without intending to be bound by any particular mechanism, it is believed that the fixation step acts to immobilize the antibody in situ.

Suitable fixatives include formaldehyde-based fixatives (e.g., formaldehyde, formalin, buffered formalin, paraformaldehyde, and the like), glutaraldehyde, and others (e.g., precipitating or extractive fixatives such as acetone, methanol/acetone, methanol/acetic acid and the like. Fixation conditions used for fixation of cells prior to conventional ICC are generally appropriate in this step. It will be appreciated that fixatives and fixation conditions are selected to avoid destruction of the ability of, e.g., an antiligand (e.g., avidin) to bind the ligand (e.g., biotin) associated with the primary antibody.

C. In Situ Hybridization

In another step of the invention, the genotype of the cell is determined by in situ hybridization of a polynucleotide probe or probes capable of specifically annealing to sequence in a cellular nucleic acid and detection of the resulting hybrid, i.e., an "in situ hybridization assay." In situ hybridization assays are well known and are generally described in Angerer et al., 1987, *Methods Enzymol.* 152: 649–660, Ausubel et al., supra, Pinkel et al., 1988, *Proc. Natl. Acad. Sci.,* 85:9138; EPO Pub. No. 430,402; Choo, ed., 1994, *Methods in Molecular Biology* Vol. 33: In Situ Hybridization Protocols, Humana Press, Totowa, N.J., and in other references listed supra, Briefly, conventional in situ hybridization assays generally comprises one or more of the following steps: (1) prehybridization treatment of the biological structure to increase accessibility of target DNA or RNA (e.g., denaturation with heat or alkali), (2) optionally (and depending on the probe) steps to reduce nonspecific binding (e.g., by blocking the hybridization capacity of repetitive sequences, e.g., using human genomnic DNA); (3) hybridization of one or more nucleic acid probes to the nucleic acid in the biological structure or tissue; (4) posthybridization washes and/or nuclease digestion to remove nucleic acid fragments not bound in the hybridization; and, (5) detection of the hybridized nucleic acid fragments. The reagents used in each of these steps and conditions for their use vary depending on the particular application.

The ISH step may be used to detect either the chromosomal DNA or mRNA of a cell. In one preferred embodiment, the detectably-labeled probe is hybridized to a chromosomal sample to detect karyotype (e.g., the presence of a Y chromosome) chromosome aberrations or chromosome number (e.g., autosomal trisomies, XXY, XYY, etc.).

ISH may be carried out using a variety of detectable or detectably labeled nucleic acid probes (e.g., $^{35}$S-labeled riboprobes, fluorescently labeled probes) capable of hybridizing to a cellular DNA (e.g., chromosomal) sequence or, alternatively, to a mRNA sequence. The probe, which may be RNA, DNA, PNA, or hybrids or chimeric molecules. As noted supra, the ISH polynucleotide probes may be labeled directly (e.g., by incorporation of fluorescently-labeled nucleotides) or indirectly (e.g., through a ligand-labeled antiligand system).

In certain embodiments, the probe is specific for a single gene (e.g., p53, HER-2/neu) or allele (e.g., p53 mutants). In other embodiments, an entire chromosome or chromosomes are stained or "painted" using probes made from highly repetitive sequences (e.g., centromeric probes) or, alternatively, using nonrepetitive sequence probes (e.g., chromosome 21 probes). When nonrepetitive probes are used it is more difficult, in conventional FISH, to achieve a high level of sensitivity and specificity. However, one limitation of centromeric probes avoided by using nonrepetitive probes is the high level of cross hybridization (e.g., between chromosome 21 centromeric sequences and chromosome 13 centromeres.

In a preferred embodiment of the present invention, the cells are treated with a formamide solution (e.g., 50% formamide in 2×SSC) before the application of the nucleic acid probe. For example, after the fixation step described in §III(B), supra, slides are washed two times 5 minutes in 70% formamide/2×SSC. Without allowing the slide to dry, probes mixed in hybridization solution (50% formamide/2×SSC) are applied onto the slide.

D. Detection of the Antibody and ISH Probes

Following the in situ hybridization step, the sample (i.e., comprising cells) is contacted with a detectably-labeled anti-ligand that binds the antibody-associated ligand described in section III(A), supra. The label associated with the anti-ligand is then be detected and the presence of the cell antigen inferred. Alternatively, the sample may be contacted with a detectably labeled or detectable secondary antibody (i.e., one that specifically binds the primary antibody bound to the cell antigen) or labeled binding molecule such as protein A, protein G, etc. to detect cells containing the target antigen (e.g., hemoglobin). The labeled or detectable secondary antibody, protein A, or protein G is then be detected and the presence of the cell antigen inferred.

The method of detection of the signals associated with the antibody probes are dependent on the specific labels or reporter groups used. In some embodiments, a microscope (e.g., a fluorescent microscope) is used to detect a precipitate, or dye (e.g., a fluorophore). When microscopic-based detection methods are used, it is often convenient to use an automated and/or computerized data collection and image analysis system. In alternative embodiments, labeled cells are detected in solution, e.g., by FACS analysis.

The annealed ISH probe is also detected following ISH, often at the same time that the antibody label is detected. The method of detecting the annealed ISH probe will also depend on the nature of the probe label. Thus, when ISH probes are labeled by incorporation of fluorescently-labeled nucleotides, detection may be accomplished by microscopic observation (manual or automatic). When detection of the ISH probe requires the application of a labeled anti-ligand (e.g. avidin-labeled rhodamine when the ISH probe is a biotinylated probe) the labeled antiligand may be added before, coincident with, or after the bound antibody is detected.

Different detectable labels (e.g., fluorescent labels with different colors or emission spectra) are selected for the antibody and the ISH probes. (It will be appreciated that if the same label is used for both antigen and chromosome sequences, it will be difficult to distinguish the signals.) Similarly, when multiple different antibody or ISH probes are used in the same sample, each probe is typically differently labeled.

It is also necessary to select the immunophenotyping reagents and an ISH labeling system that do not cross-react with each other. To illustrate this requirement, imagine a scenario in which simultaneous ICC and ISH is attempted using a biotin-labeled antibody (for ICC), a biotin-labeled polynucleotide probe (for ISH) and avidin-conjugated Texas Red for detection of the bound antibody and avidin-conjugated fluorescein for detection of the annealed polynucleotide. It will be apparent that whichever of the avidin conjugates is first added will bind both the antibody and ISH probes, rendering the results useless.

Suitable combinations of reporter molecules will be apparent to one of skill reading this disclosure. In one embodiment, fluorescent labels are used in the nucleic acid (FISH) probe and an enzymatic reporter group is used to detect the antibody staining. Illustrative embodiments are provided in Table I, infra.

TABLE I

Labeling System

| | ICC (antibody) Probe | ISH (polynucleotide) probe |
|---|---|---|
| 1 | biotin-labeled antibody + avidin-labeled fluorescent reporter molecule (e.g., fluorescein) | + digoxigenin-labled DNA probes + anti-digoxigenin labeled reporter molecule (e.g., rhodamine) |
| 2 | biotin-labeled antibody + streptavidin-labeled reporter molecule (e.g., rhodamine) | + DNA probes labeled with fluorescein-UTP. |
| 3 | digoxigenin-labled antibody + anti-digoxigenin-conjugated to enzymatic reporter molecule (e.g., HRP, alkaline phosphatase) | + DNA probes labeled with fluorescein-UTP. |

As illustrated in Table I, ISH probes may be directly labeled (e.g., incorporating a fluorescently labeled nucleotide) of indirectly labeled (e.g., incorporating a biotinylated nucleotide). Directly labeled probes have the advantage of reducing the number of steps required for detection.

When cells are screened microscopically, it is sometimes desirable to counterstain the cells, e.g., to enhance detection of nuclei. Suitable counterstains (e.g., DAPI (4'-6-diamidino-2-phenylindole) are well known.

E. Kits

It is contemplated that reagents useful for practicing the present method will be provided in kit form. In one embodiment, useful kits will include, packaged together in a container, one or more of the following reagents.

(i) an antibody specific for an antigen (e.g., a human antigen), which antibody is conjugated to a ligand (e.g., biotin or digoxigenin). In one embodiment the antigen is a fetal antigen such as ε-hemoglobin;

(ii) An anti-ligand associated with (e.g., conjugated to) a detectable label (e.g., avidin, streptavidin or anti-digoxigenin conjugated to a label such as a fluorescent label.

(iii) At least one chromosome-specific polynucleotide probe suitable for ISH. In certain one embodiment the probe is specific for chromosome X, Y, 13, 18 or 21;

(iv) Other reagents useful for the practice of the method described herein.

IV. EXAMPLES

Example 1

Detecting a Surface Antigen and the X and Y Chromosomes

Leukocytes were obtained from a normal blood sample of an adult male by histopaque centrifugation and deposited on poly-lysine microscope slides by manual smear. The cells were fixed on the slide for 10 minutes with a 2% formaldehyde/PBS (FB) solution. After further incubation with a 2% mouse serum (in PBS) solution the slides were reacted with anti-CD45 antibody conjugated with biotin (Becton-Dickinson Immunocytometry Systems, San Jose, Calif.) for 30 minutes at room temperature. The slides were washed twice and fixed in FB solution for three minutes.

Next the slides were washed two times for 5 minutes in 70% formamide/2×SSC. Without allowing the slides to dry, 10 μl of an XY DNA probe cocktail (Vysis Inc., Downers Grove, Ill.; CEP X SpectrumGreen and CEP Y SpectrumOrange DNA FISH probes) was applied to the slide and allowed to denature for five minutes at 85° C. followed by an overnight incubation at 37° C. The "XY" probe contained X probe that hybridized to the centromere region of chromosome X (Xp11.1–q11.1) and Y probe that hybridized to the centromere region of chromosome Y (Yp11.1 –q11.1) (Vysis Inc., Downers Grove, Ill.).

The slides were then washed three times 5 minutes at 46° C. in a pre-warmed solution of 50% formamide in 2×SSC, washed twice in PBS, and incubated at room temperature for 30 minutes with a 1:100 solution of streptavidin conjugated with alkaline phosphatase (Vector Inc., Burlingame, Calif.). After washing the slides twice in PBS, alkaline phosphatase substrate (Vector® Blue Alkaline Phosphatase Substrate Kit III, Vector Inc.) was added and incubated for 10 minutes at room temperature according to the manufacturers instructions. The slides were washed and mounted for observation. The slides were observed with Applied Imaging Corp. WinScan system (Applied Imaging Corp. Santa Clara, Calif.). The system is equipped with brightfield (for ICC) and fluorescence (for ISH).

Virtually 100% of the cells contained the Vector Blue stain and X, Y signals. This experiments demonstrates that carrying out ICC and FISH according to the method of the invention results in detection of antigen and genotype as accurately and efficiently as carrying out FISH alone or ICC alone according to conventional methods.

Example 2

Staining of an Intracellular Antigen and Chromosomes X, Y, and 21

Umbilical cord cells were obtained from a 10-week gestation pregnancy after termination procedures. Cells were washed to remove transport media [RPMI-1640] and fixed on a slide using FB solution. After incubation with a 2% mouse serum/PBS solution, the slides were reacted with anti-epsilon hemoglobin chain antibody conjugated with biotin (Cortex Biochem, Inc. (San Leandro Calif.) for 30 minutes at room temperature. The anti-epsilon hemoglobin antibody probe specifically identifies fetal hemoglobin. The slides were washed twice and fixed in FB solution for five minutes.

The slides were then washed twice for 5 minutes with 70% formamide/2×SSC pre-warmed to 46° C. Without letting the slides dry, 10 μl of an X, Y, 21 DNA probe cocktail (Vysis Inc., Ill.) was applied to the slide, heated to 80° C. for 8 minutes to denature the target and probe DNA, and incubated at 37° C. overnight The probe cocktail contained the following chromosome-specific probes: X chromosome- CEP X SpectrumAqua, Vysis Cat. No. 32–131023; Y chromosome: CEP Y SpectrumGreen, Vysis Cat. No. 32–132024; and 21 chromosome: LSI 21 SpectrumOrange, Vysis Cat. No. 32–190002.

The following day, the slides were washed three times five minutes in 50% formamide in 2×SSC prewarmed to 46° C. The slides were washed twice with PBS and incubated at room temperature for 30 minutes with a 1:100 solution of streptavidin conjugated with alkaline phosphatase, as described in Example 1. After washing the slides twice in PBS, alkaline phosphatase substrate (Vector Blue, Vector, Inc., Burlingame) was added and incubated for 10 minutes at room temperature. The slides were then washed and mounted for microscopic analysis. Antibody staining was calibrated on a 5-point scale (neg.=no color, 4+=intense color) according to the manufacturer's instructions.

The results of this experiment are provided in Table II, below. Approximately 42% of the cells were stained with the antibody. This proportion is consistent with the percentage of cells expected to contain epsilon hemoglobin (see, e.g., Crutcher et al., 1998, "Combination of anti-embryonic and anti-fetal hemoglobin antibodies improve identification of fetal nucleated erythrocytes" 9$^{th}$ *International Conference Prenatal Diagnosis and Therapy*, Jun. 8–11, 1998). Virtually 100% of the epsilon hemoglobin positive cells also stained positive for X, Y and 21 fluorescent signals (see rows 1–4). This represents significantly better hybridization efficiency compared to conventional methods.

In control experiments in which the antibody was omitted, no antibody staining was observed (see row 5). In controls in which the fixation after antibody binding was omitted, the number of stained cells was dramatically reduced (see row 9).

These results demonstrate high efficiency and accuracy when using non-repetitive probes (in this case, chromosome 21 unique sequence probes).

TABLE II

| | | # of Probe signals in cell | | | | | Total cells counted | Hyb. Effic. | Accuracy | Vector Blue Intensity | | | | |
|---|---|---|---|---|---|---|---|---|---|---|---|---|---|---|
| | | 0 | 1 | 2 | 3 | 4 | | | | Neg | 1+ | 2+ | 3+ | 4+ |
| 1 | Cord 8021 (XY) | | | | | | | | | | | 30 | 12 | 8 |
| 2 | X Probe | 0 | 47 | 3 | | | 50 | 100% | 94% | | | | | |
| 3 | Y Probe | 1 | 48 | 1 | | | 50 | 98% | 98% | | | | | |
| 4 | 21 Probe | 2 | 9 | 37 | 2 | | 50 | 96% | 77% | | | | | |
| 5 | Cord 8021 (XY) (No First Antibody control) | | | | | | | | | 50 | | | | |
| 6 | X Probe | 0 | 50 | | | | 50 | 100% | 100% | | | | | |
| 7 | Y Probe | 0 | 50 | | | | 50 | 100% | 100% | | | | | |
| 8 | 21 Probe | 0 | 10 | 38 | 2 | 0 | 50 | 100% | 76% | | | | | |
| 9 | Cord 8027 (XY) (No fix control) | | | | | | | | | 16 | 7 | 15 | 11 | 1 |
| 10 | X probe | 0 | 50 | | | | 50 | 100% | 100% | | | | | |
| 11 | Y Probe | 0 | 50 | | | | 50 | 100% | 100% | | | | | |
| 12 | 21 probe | 3 | 13 | 31 | 3 | 0 | 50 | 94% | 66% | | | | | |

Example 3

Staining of an Intracellular Antigen and Chromosomes X, 13, and 18

HeLa cells were deposited on a slide and fixed for 2 min with a 1:1 (v/v) methanol acetone solution for two minutes followed by two wash cycles in PBS. After incubation with a solution of 2% mouse serum in PBS, the slides were reacted with anti-cytokeratin antibody conjugated with biotin (DAKO, Carpinteria, Calif.) for 30 minutes at room temperature.

The slides were washed twice and the cells fixed for 2 minutes in methanol/acetone (1:1). Next the slides were washed two times 5 minutes at 46° C. in a pre-warmed solution of 70% formamide/2×SSC. Without letting the slides dry, 10 μl of an X, 13, 18 DNA probe cocktail (Vysis Inc., Ill.) was applied to the slide, the probe was allowed to denature for eight minutes at 80° C. followed by an overnight incubation at 37° C. The probe cocktail contained the following probes: X chromosome- CEP X SpectrumAqua, Vysis Cat. No. 32–131023; chromosome 13- LSI 13 (RB1, 13q14) SpectrumOrange, Vysis cat. no. 32-190001; chromosome 18- CEP 18(alpha satellite, D18Z1) SpectrumGreen, Vysis cat. no. 32-132018. The Vysis chromosome 13 probe contains unique DNA sequences spanning the RB1 gene located within band 13q14 on the long arm of chromosome 13. The chromosome 18 probe hybridizes to the centromere region (alpha satellite D18Z1) of chromosome 18 (18p11.1–q11.1).

The following day, the slides were washed three times at 46° C. for five minutes each wash in a pre-warmed solution of 50% formamide in 2×SSC. The slides were then washed twice with PBS and incubated at room temperature for 30 minutes with a 1:100 solution of streptavidin conjugated with alkaline phosphatase. After washing the sl des twice in PBS alkaline phosphatase substrate (Vector Blue, Vector, Inc., Burlingame) was added and incubated for 10 minutes at room temperature. The slides were then washed and mounted for observation The results of this experiment are summarized in Table III, below. Virtually 100% of the cells staining positive for cytokeratin (i.e., HeLa cells) showed X, 13, and 18 fluorescent signals.

TABLE III

| No. of Probe Signal | 1 | 2 | 3 | 4 | 5 | 6 | 7 | 8 | 9 | Total Cells |
|---|---|---|---|---|---|---|---|---|---|---|
| X | 6 | 21 | 37 | 2 | 0 | 0 | 0 | 0 | 0 | 66 |
| 13 | 7 | 29 | 25 | 3 | 2 | 0 | 0 | 0 | 0 | 66 |
| 18 | 3 | 16 | 44 | 1 | 1 | 1 | 0 | 0 | 0 | 66 |

| Chromosome | No. of Chromosome | % of Cells | Range of Chromosome |
|---|---|---|---|
| 13 | 2 | 44 | 1–5 |
| 18 | 3 | 67 | 1–6 |
| X | 3 | 56 | 1–4 |

The copy number for each chromosome detected in cytokeratin-positive cells using this method was consistent with the number expected (as detailed below). Thus, these results correspond the reported ranges, with many cells having generally higher numbers of detectable chromosomes. The detection of generally higher chromosomes copy numbers using the present method than reported using prior art methods indicates that the present method is very sensitive.

Previously Reported HeLa Cell Chromosome Numbers

The copy number of chromosome 13 in HeLa cells was reported a 1 (Lin and Godstein, 1974, "Analysis of Q-banding patterns in human cell lines" *J. Natn. Cancer Insti.* 53:298–304); and Heneen, 1976, "HeLa cells and their possible contamination of other cell lines" *Hereditas* 82:217–248 or 2 (Wang and Fedoroff, 1973, "Karyology of cell in culture: trypsin technique to reveal G-band," in Kruse P. Jr. Patterson M. K. Jr. (eds): Tissue Culture Methods and Application, pp. 782–787 (Academic Press, New York); Kraemer et al., 1973, "On the nature heteroploidy" *Cold Spring Harb Symp Quant Biol* 38:133–144.; Nelswon-Rees et al., 1974, "HeLa-like chromosomes and type A variant G6PD isoenzyme in human cell culture producing Mason-Pfizer monkey virus-like particles" *J. Natn. Cancer Inst.* 53:751–757; and Mamaeba, 1983, "Cytogenetics and tissue culture," in Troshin AS (ed): Biology of the Cell in culture, pp 195–234). Chen, 1988, "Re-evaluation of HeLa, HeLa S3, and HEP-2 karyotypes" *Cytogenet Cell Genet* 48: 19–24 reported that 54% of HeLa cells had 2 copies of chromosome 13 and 46% had 3 copies.

The copy number of chromosome 18 in HeLa cells was reported as 1 by Nelson-Rees et al., supra, 2 by Kraemer et al., supra and Lin and Goldstein, supra (1974), 3 by Wang and Fedoroff, supra, Heneen, 1976, supra; Mamaeba, supra, and Chen, supra.

The copy number of chromosome 21 in HeLa cells was reported as 1 by Kraemer et al supra, 2 by Lin and Goldstein, supra, and Mamaeba supra, 3 by Wang and Fedoroff supra, and Heneen, supra, and 4 by Nelson-Rees et al. supra,. Chen (1988) reported that 90% of HeLa cells had 2 copies of chromosome 21 with the range of 1 to 3 copies.

The number of chromosome X of HeLa cells was identified to be 1 by Lin and Goldstein (1974), 2 by Wang and Fedoroff (1973), Kraemer et al. (1973), Nelson-Rees et al. (1974), Heneen (1976) and Mamaeba (1984). Chen (1988) reported that 76% of HeLa cells had 3 copies of chromosome X and 24% had 2 copies.

Example 4

Staining of an Intracellular Antigen and Chromosomes X and 21

HeLa cells were mixed with XY peripheral blood lymphocytes (1:1000) and contacted with anti-cytokeratin antibody probes as described in Example 3, supra. ISH was carried out using chromosome 21 and X -specific probes as described in Example 2, supra. Virtually all of the HeLa cells (but no lymphocytes) stained positive for cytokeratin. The of the ISH staining are provided in Table IV, infra.

TABLE IV

| No. of Probe Signals | 1 | 2 | 3 | 4 | 5 | 6 | 7 | 8 | 12 | Total Cells |
|---|---|---|---|---|---|---|---|---|---|---|
| X | 9 | 34 | 67 | 10 | 2 | 0 | 1 | 0 | 1 | 124 |
| 21 | 6 | 37 | 66 | 8 | 5 | 0 | 1 | 0 | 1 | 124 |

| Chromosome | No. of Chromosome | % of Cells | Range of Chromosome |
|---|---|---|---|
| 21 | 3 | 53 | 1–12 |
| X | 3 | 54 | 1–12 |

These results show that when HeLa cells were diluted with male lymphocytes, the HeLa cells can be detected and their genotype and phenotype can be accurately determined.

All references cited herein are incorporated herein by reference in their entirety and for all purposes to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of simultaneously determining a cell phenotype and genotype comprising:
   (a) contacting the cell with an antibody bound to a ligand, wherein the antibody is specific for an antigen suspected of being associated with the cell;
   (b) contacting the cell with polynucleotide probe under conditions that allow the probe to hybridize to a target sequence in a cellular nucleic acid, thereby forming a complex of the polynucleotide probe and cellular nucleic acid;
   (c) contacting the cell with a detectably labeled anti-ligand under conditions where the detectably labeled anti-ligand binds to the ligand;
   (d) detecting the presence of the labeled anti-ligand;
   (e) detecting the presence of the complex of the polynucleotide probe and cellular nucleic acid; and,
   (f) correlating the presence of the anti-ligand with the presence of the antigen in the cell thereby determining the cell phenotype, and correlating the presence of said complex of the polynucleotide probe and cellular nucleic acid with the presence of the target sequence in the cell, thereby determining the cell genotype;
   wherein said step (a) precedes step (b), and step (b) precedes step (c).

2. The method of claim 1, wherein the cell is exposed to a fixative between step (a) and step (b).

3. The method of claim 1 wherein the cell is a human fetal cell.

4. The method of claim 1 wherein the antibody is monoclonal.

5. The method of claim 1 wherein the ligand is biotin and the anti-ligand is avidin or streptavidin.

6. The method of claim 1 wherein the anti-ligand is labeled with a reporter molecule that is fluorescent, a radioisotope, or an enzyme.

7. The method of claim 1 wherein the antigen is a hemoglobin.

8. The method of claim 1 wherein the polynucleotide probe is DNA.

9. The method of claim 1 wherein the polynucleotide probe specifically hybridizes to sequences of human chromosomes X, Y, 13, 18 or 21.

10. The method of claim 1, wherein detecting the labeled antiligand in step (d) comprises microscopic detection of a signal from the label.

11. The method of claim 1, wherein detecting the presence of the complex of the polynucleotide probe and cellular nucleic acid in step (e) comprises microscopic detection of a signal associated with the polynucleotide probe.

12. The method of claim 1 wherein the cell is a fetal cell, a malignant cell, or a cell suspected of being malignant.

13. A method of diagnosing a fetal abnormality comprising carrying out the process of claim 1, wherein the cell is a human fetal cell.

14. A method of simultaneously determining a cell phenotype and genotype comprising:
   (a) contacting the cell with d antibody specific for an antigen suspected of being associated with the cell;
   (b) contacting the cell with polynucleotide probe under conditions that allow the probe to hybridize to a target sequence in a cellular nucleic acid, thereby forming a complex of the polynucleotide probe and cellular nucleic acid;
   (c) contacting the cell with a binding molecule that specifically binds the antibody of step (a);
   (d) detecting the presence of the binding molecule;
   (e) detecting the presence of the complex of the polynucleotide probe and cellular nucleic acid; and,
   (f) correlating the presence of the binding molecule with the presence of the antigen in the cell thereby determining the cell phenotype, and correlating the presence of said complex of the polynucleotide probe and cellular nucleic acid with the presence of the target sequence in the cell, thereby determining the cell genotype;
   wherein said step (a) precedes step (b), and step (b) precedes step (c).

15. The method of claim 14, wherein the cell is exposed to a fixative between step (a) and step (b).

16. The method of claim 14 wherein the binding molecule is an anti-immunoglobulin antibody, protein A or protein G.

17. The method of claim 15 wherein the anti-immunoglobulin antibody, protein A or protein G is detectably labeled.

18. The method of claim 17 wherein the detectable label is a reporter molecule that is fluorescent, a radioisotope, or an enzyme.

19. The method of claim 14 wherein the cell is a human fetal cell.

20. The method of claim 14 wherein the antibody is monoclonal.

21. The method of claim 14 wherein the antigen is a hemoglobin.

22. The method of claim 14 wherein the polynucleotide probe is DNA.

23. The method of claim 14 wherein the polynucleotide probe specifically hybridizes to sequences of human chromosomes X, Y, 13, 18 or 21.

24. The method of claim 14, wherein detecting the binding molecule in step (d) comprises microscopic detection of a signal associated with the binding molecule.

25. The method of claim 14, wherein detecting the presence of the complex of the polynucleotide probe and cellular nucleic acid in step (e) comprises microscopic detection of a signal associated with the polynucleotide probe.

26. The method of claim 14 wherein the cell is a fetal cell, a malignant cell, or a cell suspected of being malignant.

27. A method of diagnosing a fetal abnormality comprising carrying out the process of claim 14, wherein the cell is a human fetal cell.

* * * * *